US011953433B2

(12) United States Patent
Kirchmann et al.

(10) Patent No.: US 11,953,433 B2
(45) Date of Patent: Apr. 9, 2024

(54) METHOD FOR ANALYSING PROCESS STREAMS

(71) Applicant: hte GmbH the high throughput experimentation company, Heidelberg (DE)

(72) Inventors: Marius Kirchmann, Heidelberg (DE); Christoph Hauber, Heidelberg (DE)

(73) Assignee: hte GmbH the high throughput experimentation company, Heidelberg (DE)

(*) Notice: Subject to any disclaimer, the term of this patent is extended or adjusted under 35 U.S.C. 154(b) by 869 days.

(21) Appl. No.: 16/978,333

(22) PCT Filed: Mar. 15, 2019

(86) PCT No.: PCT/EP2019/056537
§ 371 (c)(1),
(2) Date: Sep. 4, 2020

(87) PCT Pub. No.: WO2019/179887
PCT Pub. Date: Sep. 26, 2019

(65) Prior Publication Data
US 2021/0003502 A1    Jan. 7, 2021

(30) Foreign Application Priority Data
Mar. 20, 2018   (EP) .................................... 18162722

(51) Int. Cl.
*G01N 21/61* (2006.01)
*G01N 21/3504* (2014.01)
(Continued)

(52) U.S. Cl.
CPC ......... *G01N 21/3504* (2013.01); *G01N 21/85* (2013.01); *G01N 30/02* (2013.01);
(Continued)

(58) Field of Classification Search
None
See application file for complete search history.

(56) References Cited

U.S. PATENT DOCUMENTS

| 5,349,188 A | 9/1994 | Maggard |
| 5,360,972 A | 11/1994 | Difoggio et al. |

(Continued)

FOREIGN PATENT DOCUMENTS

| JP | H0232253 | 2/1990 |
| WO | WO-99/02973 A1 | 1/1999 |

(Continued)

OTHER PUBLICATIONS

International Search Report for International Application No. PCT/EP2019/056537 dated Jul. 22, 2019, 8 pgs.
European Search Report for EP Patent Application No. 18162722.5, dated Oct. 24, 2018, 4 pages.

*Primary Examiner* — Hoon K Song
(74) *Attorney, Agent, or Firm* — Element IP, PLC

(57) ABSTRACT

The invention relates to a method for investigating process streams comprising five or more different hydrocarbon-containing components. In the method at least one process flow line (35) is in operative connection with an online IR spectrometer (2) and an online gas chromatograph (1). The process stream passed through the process stream conduit (35) is subjected to an online characterization which comprises measurements both with the online IR spectrometer and with an online gas chromatograph. The spectral data and the chromatography data are mathematically related to one another by suitable statistical models, thus allowing training of a model used for evaluating the analytical data and for characterizing the process streams. The method according to the invention is characterized by short measurement times in the range of seconds and milliseconds and a high accuracy. The method according to the invention for investigating process streams preferably relates to investigation of process (Continued)

streams deriving from processes proceeding in parallel, the process streams preferably deriving from reaction spaces arranged in parallel.

15 Claims, 9 Drawing Sheets

(51) Int. Cl.
| | | |
|---|---|---|
| *G01N 21/85* | (2006.01) | |
| *G01N 30/02* | (2006.01) | |
| *G01N 33/28* | (2006.01) | |
| *G06N 20/00* | (2019.01) | |
| *G01N 21/84* | (2006.01) | |
| *G01N 30/88* | (2006.01) | |

(52) U.S. Cl.
CPC ......... *G01N 33/2829* (2013.01); *G06N 20/00* (2019.01); *G01N 2021/8411* (2013.01); *G01N 2030/025* (2013.01); *G01N 2030/8886* (2013.01)

(56) References Cited

U.S. PATENT DOCUMENTS

| | | |
|---|---|---|
| 5,596,196 A | 1/1997 | Cooper et al. |
| 2002/0031737 A1 | 3/2002 | Von Drasek et al. |
| 2002/0182735 A1 | 12/2002 | Kibby et al. |
| 2004/0084623 A1* | 5/2004 | Long .................... G01N 21/359 250/341.2 |
| 2007/0082407 A1 | 4/2007 | Little |
| 2015/0260695 A1 | 9/2015 | Spartz et al. |
| 2015/0338546 A1* | 11/2015 | Bright .................... G01N 21/61 250/255 |
| 2016/0046529 A1* | 2/2016 | Bricco .................... E21B 15/00 175/425 |
| 2019/0390524 A1* | 12/2019 | Bentamy ............ G01N 33/0011 |

FOREIGN PATENT DOCUMENTS

| | | |
|---|---|---|
| WO | WO-01/02088 A1 | 1/2001 |
| WO | WO-2016/110408 A1 | 7/2016 |
| WO | 2017/075140 | 5/2017 |

\* cited by examiner

METHOD FOR ANALYSING PROCESS STREAMS

The present invention relates to a method for investigating process streams whose composition changes in short time intervals. The method according to the invention is flexible and versatile. A preferred field of application of the method relates to catalytic processes comprising product streams having a large number of components, in particular comprising five or more different hydrocarbon-containing components.

The catalytic processes of interest here are characterized in that they are carried out in industrial production operations and in flow reactors. In numerous processes, complex reaction networks are formed in the catalyst beds of the reactors. The term "complex reaction networks" in the context of the present invention is to be understood as meaning that the reactions proceeding in the reactors can no longer be described by simple chemical reaction mechanisms, for example first-order kinetics, and a large number of reactions take place simultaneously in the catalyst bed. This results in process streams having a composition comprising a multiplicity of different components.

The complexity that characterizes these process streams also results from the fact that the compositions of the process streams can change in comparatively short periods of time, within hours, minutes and seconds. The reasons for these changes are, for example, deactivation or running-in behavior of the catalysts, changes in the composition of starting materials or changes in process conditions.

Online spectroscopic methods for characterizing complex sample mixtures by chemometric methods in industrial production processes are known in principle in the prior art. A brief overview of the prior art is given below.

In the petrochemical sector and in the blending of fuels, spectroscopic analysis methods for determining the composition of process streams have been in use for several decades. The fuels may comprise several hundred different compounds and the target composition of the fuels must be in a very narrow range in order for them to provide the desired properties in terms of knock resistance. Since the refineries produce large amounts of fuels, the spectroscopic methods are particularly suitable for determining the chemical composition of the streams at short intervals. One example in the blending of oxygenate-containing hydrocarbons is U.S. Pat. No. 5,596,196 which discloses that oxygenate-containing hydrocarbons may be determined with high precision using Raman spectroscopy and multivariate analysis. The resulting measurement signals may be used to control the concentration of the components in the products. This method is performed directly in the process stream in the liquid phase using glass fiber optics and can provide measurement values in less than one minute.

PCT application WO 01/02088 A1 describes a method for controlling the production process of polyhydroxy alcohols. In this method the composition of the liquid process stream is continuously monitored using IR spectroscopy. The difference between the measured composition and the desired composition is then determined in order to control the parameters of the production process. The process is a multi-stage process. Measurements may be taken at different points in the process stream. The absorbance of the process stream is measured by means of an IR spectrometer, before a computer determines the composition of the process stream in accordance with a previously programmed calibration model.

An example in the context of blends of liquid process streams is U.S. Pat. No. 5,349,188, Ashland Oil Inc, which addresses NIR analysis of PIANO constituents and determination of the octane number of hydrocarbons. PIANO constituents comprise the groups paraffins, isoparaffins, aromatics, naphthenes and olefins. The method comprises measuring the absorption bands characteristic for the group of the individual PIANO constituents.

Ashland Oil Inc. also disclosed in WO 99/02973 a process/apparatus for the investigation of hydrocarbons using NIR, wherein concentrations of individual components in the aromatic range (BTX) are correlated with specific absorption bands in the NIR spectrum using statistical methods, thus allowing measurement and process control in the liquid phase in refinery processes.

U.S. Pat. No. 5,360,972, Western Atlas International Inc., discloses the improvement of IR-spectroscopic measurements on materials achieved by analysis of the spectroscopic data with calibration models. Different mathematical calibration models are described. In connection with performance of the investigations it is described that measurements on standard samples are undertaken, an NEG calibration set being used here. The standard samples are liquid samples analyzed with a GC analyzer operated independently of a process stream.

In summary it may be noted that the prior art is preferably operated in the liquid phase and in large industrial scale plants. For the calibration of the spectroscopic method (MIR, NIR, Raman), samples are analyzed offline, i.e. outside the actual course of the reaction and the test conditions, using gas or liquid chromatography and then also measured spectroscopically. Based on this offline calibration a model is developed using statistical methods and the spectroscopic analysis is subsequently carried out online, i.e. under the actual reaction conditions, in the process stream.

US 2007/0082407 A1, Joseph P. Little, describes and claims performing an online analysis of a process stream based on the use of an optical analyzer. The optical analyzer includes a number of optical sensors that may be used to perform spectroscopic analyses. The spectroscopic analyses are used to determine the chemical composition of natural gas. The sensors are integrated into a data collection system to determine the composition of natural gas at different locations within a storage and transmission infrastructure in virtually continuous fashion.

JPH0232253, Shimadzu Corp., describes an apparatus allowing the processing of data, wherein the detector signals from the chromatograph and the spectrometer are subjected to real-time data processing.

US 2015/0260695 A1, Prism Analytical Tech. Inc., describes and claims a measuring instrument consisting of a combination of a gas chromatograph and an FTIR spectrometer. The FTIR spectrometer is connected downstream of the separating column of the gas chromatograph. Use of the instrument comprises first separating the sample into its individual components and supplying the individual components into an IR measuring cell.

WO 2017/075140 A1 is also from the same applicant as US 2015/0260695 A1, i.e. from Prism Analytical Tech. Inc., and describes and claims a measurement means consisting of a combination of a gas chromatograph and FT IR spectroscopic analysis.

US 2002/0031737 A1 from American Air Liquid Inc. describes a method and an apparatus for using a tunable laser diode to investigate specific components in a gas flow from a process conduit, wherein the investigations are carried out on combustion processes in real-time. The investigations relate to the species $O_2$, CO, $H_2O$. The field of application is thus limited to just a few components.

In a preferred embodiment the method according to the invention is used in the field of high-throughput research. The field of high-throughput research relates to the acceleration and parallelization of research experiments. Improving catalytic processes and catalysts by means of high-throughput research is particularly important since the improvements help to save energy and/or conserve resources.

Prior art in the field of high-throughput research that may be mentioned includes US application US 2002/0182735 A1, Kibby et al., or else PCT application WO 2016/110408 A1, Kirchmann et al. US 2002/0182735 A1 describes the use of microreactors in combinatorial chemistry. The products produced during the reactions can be investigated and tested with regard to different properties, these properties also including octane number and cetane number. Once the reaction is complete the reaction products may be individually transferred from a channel to an analytical measuring instrument, in particular to a chromatograph.

PCT application WO 2016/110408 A1 by Kirchmann et al., which originates from the same applicant as the present application, relates to an apparatus and a method for investigating naphtha reforming processes. The apparatus comprises a multiplicity of reactors arranged in parallel. The output conduits from the reactors are connected to an online gas chromatograph. The gas chromatographic analysis of the product fluid streams is used to optimize the reaction processes proceeding in the individual reactors arranged in parallel.

It is an object of the present invention to provide a method for investigating process streams, in particular process streams whose composition may change over time, in particular over relatively short time intervals. The method according to the invention should also make it possible to monitor changes in the composition of the process streams occurring in the abovementioned short time intervals. It is a further object to provide a method which is preferably employable in high-throughput research, wherein the method makes it possible to investigate a plurality of processes performed in a parallel arrangement. It is yet a further object to provide a method for investigating catalysts, in particular for parallel investigation of catalysts under reaction conditions as close as possible to in-practice reaction conditions.

These and other objects are achieved by a method for investigating at least one process stream comprising at least five different hydrocarbon-containing components, wherein the method comprises at least the steps of:
a) providing at least one process stream conduit (35) which is in operative connection with at least one online IR spectrometer (2) and in operative connection with at least one online gas chromatograph (1),
b) passing at least one process stream through the at least one process stream conduit (35), wherein during this passing of the process stream through the process stream conduit (35) an analytical characterization of the process stream using an online IR spectrometer (2) and an online gas chromatograph (1) is performed.

Step b) is preferably carried out over a time window of less than 1 hour, preferably less than 40 minutes.

The method according to the invention combines the advantages of chromatography (high depth of detail) and spectroscopy (rapidity). Both are employed directly in the product stream online, i.e. during the catalytic conversion, either simultaneously or sequentially with a known time offset. One advantageous aspect of the method according to the invention is the use of an online gas chromatographic method since online gas chromatography makes it possible to undertake separation of the reaction products into their individual chemical compounds and provides detailed qualitative and quantitative analysis. The gas chromatographic analysis provides the relevant information on chemical composition, namely with reference to individual components and the amount of the individual components. This information makes it possible to derive the target parameters.

These target parameters are preferably parameters selected from the group of conversion, octane number and selectivity.

However, chromatography also has the property that it delivers these results with a time offset which, especially for complex process streams, may be in the range of 20 to 180 min and may be too slow to capture rapid changes in the product streams.

By contrast, spectroscopic methods provide information in the form of absorption as a function of the wavenumber, wherein each spectrum provides characteristic bands belonging to a specific substance concentration and time. The advantage of spectroscopic methods is that the results are available quasi-simultaneously, thus allowing virtually continuous analysis. The measurement time of the online spectroscopic analysis may be in the seconds range. The method according to the invention thus makes it possible to achieve a temporal resolution in the range of seconds.

A spectroscopic method may thus be used to achieve rapid regulation, wherein upon achieving a target parameter, and to record measurement data having a high information density, chromatographic methods are employed to obtain more details.

The use of a spectroscopic analytical method is generally associated with high calibration cost and complexity. The evaluation of complex process streams especially requires calibration using a chemometric model.

One advantage of the method according to the invention is that the method may be carried out under process conditions which correspond to the process conditions of real (i.e. reaction conditions actually occurring when the reaction is carried out on an industrial scale) process streams.

The method according to the invention is preferably used to investigate processes which proceed in a time window of 5 sec-30 days, more preferably in a time window of 30 sec-14 days, yet more preferably 60 sec-7 days, and which can no longer be tracked over time with chromatographic methods commonly used on an industrial scale or in which the use of controls loops for readjustment can no longer be carried out quickly enough to track changes in the product spectrum.

However, it is also possible to employ the method according to the invention in connection with the investigation of process streams present for periods longer than 30 days, for example the method can also be carried out in connection with process streams where the time window is in the range of 2-24 months.

The method according to the invention has the advantage that the GC measurement method and the IR spectroscopic measurement method are performed in situ, i.e. directly in the process stream. The calibration of the GC measurement method and the calibration of the IR-spectroscopic measurement method and the correlation of both measurement methods are preferably performed based on in situ measurements. The method is more preferably operated as a self-learning system. In this preferred embodiment of the self-learning system the method is characterized in that the method is performed without sample analyses analyzed outside the process stream.

It should be noted that the method according to the invention comprises the combination of different analytical methods that are in direct operative connection with the process stream. The resulting analyses are based on virtually identical samples of the process stream. This results in synergy effects with regard to the sensitivity of the method according to the invention. Further technical advantages are associated with the feedback brought about by the fact that the process control may be operated using the data.

By contrast, instruments used as off-line instruments are independent of the process stream conduit and also have no connection to the process stream. Such instruments operated as an off-line instrument, i.e. in an ex situ method/outside the process stream, therefore cannot be used to analyze the process stream by an in situ method.

In a preferred embodiment, the analysis units, the online gas chromatograph (1) and the online IR spectrometer (2), are coupled to a common process control unit (4), wherein the process control unit is in operative connection with a process space (11) and controls, governs or regulates the process proceeding in the process space.

The method is preferably performed to investigate process streams in which the number of hydrocarbon-containing components in the individual process streams is ≥5, the number of hydrocarbon-containing components in the individual process streams more preferably being ≥5 to 300. It is yet more preferable when the number of hydrocarbon-containing components in the individual process streams is ≥10 bis 250.

A preferred embodiment concerns a method further comprising the steps of:
c) evaluating the spectral data obtained in the analytical characterization of the process stream using an online IR spectrometer as a function of the time at which this spectroscopic analysis of the process stream was carried out,
d) evaluating the chromatography data obtained during the analytical characterization of the process stream using the online gas chromatograph as a function of a sampling time for samples taken from the process stream,
e) machine learning-based training of a model that models a mathematical relationship between spectral data and corresponding chromatography data in respect of an identical process stream by using the evaluation results obtained in steps c) and d) in respect of the process stream passed through the process stream conduit in step b).

It is preferable when the training of the model takes place in situ as it were, i.e. during the reaction or during the process. This has the advantage that an external calibration, which can be costly and complex, is unnecessary. The training of the model thus takes place in-situ during the reaction, and complex external calibration is not necessary. The model may be adapted and supplemented for each new process stream or a new model may be trained and the risk of overfitting is minimized.

Such a training dataset is preferably obtained as follows:
1) Fast changing of the process stream <30 min: Performing the reaction under comparatively "mild" process conditions which do retard the speed of change but nevertheless provide representative product compositions (low WHSV, temperature, . . . ). Optionally also additional variation of the process parameters to obtain a wider range of product compositions.
2) Slow changing of the process stream >30 min: It would be possible in principle to use exclusively GC in the case of the reaction proceeding slowly but rapid analysis offers opportunities to increase the degree of parallelization or to capture different product streams or, when regulating to a target parameter, to reach said parameter more quickly.

In embodiments of the method according to the invention, after obtaining the training dataset in step e) or according to steps c)-e) the chromatographic method used to determine the product composition may be paused and the measurement is carried out exclusively via the spectroscopic method. (However, gas chromatography can be used for spot checks).

During a training phase the analysis results collect representative ranges of compositions of the process stream which may be supplemented by varying process parameters such as temperature, pressure, WHSV or the starting material composition.

In the case of (excessively) fast changing of the process stream which would result in insufficient temporal resolution for gas chromatographic analytical methods, the deactivation can be retarded by suitable variation of process parameters (for example by variation of WHSV, T, $H_2$ partial pressure, water vapor addition, etc.).

Particular preference is given to one embodiment of the method in which, preferably during the training phase, steps c)-e) are performed and at least one reaction parameter is altered in relation to the same reaction parameter as set in steps a) and/or b), wherein this parameter is preferably selected from: WHSV, temperature, total pressure and/or partial pressure of reactants. Specific alteration of the reaction parameters allows the reaction rate or the conversion to be reduced or increased.

These reaction parameters or process parameters are preferably one or more parameters selected from the group of WHSV, T, total pressure, partial pressures of the reactants, addition of co-feed molecules, for example water as a co-feed molecule. Characterizing the process stream obtained for a set of process parameters in each case affords a dataset comprising analytical characterization data which is characteristic of the respective parameter space.

It is preferable when the process parameters are in a process parameter space which is of technical importance for the method investigated in each case.

The temperature of the process coupled with the method according to the invention is preferably in a range of 50° C.-1000° C., more preferably in a range of 150° C.-750° C., yet more preferably in a range of 250° C.-650° C.

The pressure of the process is preferably in a range of 0.5-500 bar, more preferably in a range of 1-250 bar, yet more preferably in a range of 5-200 bar. The presently recited pressure relates to the absolute pressure value or (d.h. p.a.).

The WHSV is preferably in a range of 0.01-500 $h^{-1}$, more preferably in a range of 0.5-20 $h^{-1}$, yet more preferably in a range of 1-5 $h^{-1}$.

In a preferred embodiment the method according to the invention is characterized in that it comprises at least two different phases, wherein one phase is a training phase comprising steps a) to e) and the second phase is an actual measurement phase in which an analytical characterization of a process stream passed through the at least one process stream conduit is carried out using the online IR spectrometer (2) on the basis of the model trained in the training phase.

In a preferred embodiment the method according to the invention distinguishes between a training phase and a measurement phase. In the measurement phase all reaction parameters are typically in a target parameter space. By contrast, in the training phase the reaction parameters are typically not yet in the target parameter space or at least one reaction parameter is varied in a controlled manner to generate a representative range of different process streams having different compositions.

In the method according to the invention it is also preferable when the process stream passed through the process stream conduit is a gaseous process stream, the temperature of the gaseous process stream preferably being in the range of 20-350° C., more preferably in the range of 50-220° C. The temperature controlling of the process stream conduit ensures that the hydrocarbon-containing components in the process stream are in the gas phase. This makes it possible to save the time required for condensation of the hydrocarbon-containing components. In preferred exemplary embodiments the temperature is adjusted so as to obtain a signal-to-noise ratio in which the couplings of vibrational bands are reduced.

In the case where the online gas chromatograph (1) and the online IR spectrometer (2) are arranged serially in respect of the process stream conduit it is preferable when the measurements are performed with a temporal offset, wherein the temporal offset is in the range of 1 sec to 180 sec.

Preference is given to an embodiment of the method according to the invention in which the method comprises a feedback. In a preferred embodiment, the method is characterized in that the analysis units, the online gas chromatograph (1) and the online IR spectrometer (2), are coupled to a common process control unit (4), wherein the process control unit (4) is in operative connection with a process space (11) and controls, governs or regulates the process proceeding in the process space. The determined measurement data are used to govern, regulate or control the process. The short measurement times are of particular advantage since this results in a rapid feedback that is in the range of the duration of the online IR measurement. The reason for this is that the duration required for processing the data and transferring regulating or control signals to process units is very short and takes only milliseconds.

It is preferable when the process control unit (4) regulates the process such that the product structure is controlled by adapting a process operating parameter, the product structure preferably being controlled in such a way that octane number is constant, that selectivity is constant or that conversion is constant, regulation more preferably being undertaken by altering parameters from the group of temperature and WHSV.

The method for investigating at least one process stream is preferably employed for investigating a process stream derived from the group selected from methanol conversion processes such as MTO (for example methanol to olefins), dehydrogenation reactions (for example propane dehydrogenations), coupling reactions (for example methane couplings), naphtha reforming and processes for synthesis and conversion of aromatics (for example transalkylations, alkylations, dealkylations).

The method for investigating at least one process stream preferably employs as the online IR spectrometer (2) an instrument which operates in the mid IR range (MIR) and in which the wavenumbers are in the range of 400 $cm^{-1}$-3500 $cm^{-1}$.

In the method according to the invention for investigating at least one process stream it is also preferable when the model or the method as employed in step e) comprises a statistical method selected from the group of multivariate analyses such as principal component analysis (PCA), partial least squares (PLS) regression, principal component regression (PCR), multi-linear regression (MLR) analysis, discriminant analysis or neural networks. Correlation of the achieved analytical results, achieved by online IR spectroscopy and online gas chromatography, is carried out by relating the analytical results to one another via suitable statistical methods and training a model. Suitable static methods are for example those selected from the group of multivariate analyses such as principal component analysis (PCA), partial least squares (PLS) regression, principal component regression (PCR), multi-linear regression (MLR) analysis, discriminant analysis or neural networks.

In the method according to the invention for investigating at least one process stream it is further preferred when additional data for training the model, provided for according to steps c) to e), are obtained by variation of process parameters such as temperature, pressure, partial pressure of the reactants or WHSV.

In a preferred embodiment the method for investigating at least one process stream relates to a process stream deriving from a catalytic process in which a solid catalyst is arranged inside the process space, wherein the mass of the solid catalyst arranged inside the process space is in the range of 0.1-200 ccm, preferably between 0.2-20 ccm.

The present invention also relates to the use of the method according to the invention in the different embodiments recited in the context of the present description for high-throughput testing of at least four, preferably at least eight, more preferably at least twelve, catalysts arranged in parallel reactors.

When operating high-throughput equipment the use of powerful analytical methods is of interest to capture the reaction products qualitatively and quantitatively. In a preferred embodiment the method according to the invention is employed in high-throughput testing and in connection with the investigation of catalysts. Here too it is preferred when the catalysts are present in process spaces arranged in parallel.

The process spaces are preferably reactors and the reactors preferably have catalysts arranged in them. The method according to the invention is preferably performed for investigating process streams where the process stream conduit (35) is in operative connection with four reactors arranged in parallel. It is more preferable when the process stream conduit (35) is in operative connection with at least eight reactors arranged in parallel, more preferably to at least twelve reactors arranged in parallel and yet more preferably to sixteen reactors arranged in parallel. The reactors are preferably tubular reactors.

The combination of the method according to the invention in conjunction with high-throughput research and high-throughput apparatuses constitutes a preferred embodiment because it brings about synergy effects, for example such that data sets recorded during the training phase or the calibration phase may be employed in a shorter time and with improved efficiency. The process spaces, preferably reactors, arranged in parallel and laden with different catalysts provide process streams that have differences and may be used for calibration. Parallel performance makes it possible to integrate the calibration phase into the measurement method.

The use of the method according to the invention is particularly advantageous in conjunction with a high-throughput apparatus, since the method exhibits great flexibility with regard to the chemical process and the high-throughput apparatus is simple to repurpose if it is to be repurposed from one chemical reaction process to another chemical reaction process, as is often the case in research especially.

The method according to the invention makes it possible to investigate reaction networks and processes with improved data depth and to better understand mechanisms of catalyst deactivation which might form the basis for development of better catalysts and could therefore lead to savings in energy and resources.

In a preferred embodiment the method according to the invention for investigating process streams additionally further comprises one or more process steps for regenerating deactivated catalyst.

The regeneration preferably removes deposits that have been deposited on the catalyst. Removal of the deposits may be achieved for example by increasing the temperature of the catalyst or the deposits may be burnt off in the presence of an oxygen-containing gas stream. In investigations into combustive coke removal the analysis may specifically be targeted to product components CO, $CO_2$ and $H_2O$.

In a preferred embodiment the method is used for investigating reaction kinetics. It is further preferred to employ the method in connection with processes having short contact times or short deactivation times.

In preferred embodiments the IR measurement time per measurement point is ≤10 sec, ≤5 sec, ≤2.5 sec, ≤1.25 sec. The term IR measurement time relates to the total measurement duration and includes the time for scanning and the time for data evaluation.

In embodiments, in particular for kinetics investigations, the IR measurement time per measurement point is in the range of tenths of a second, wherein scans are initially only recorded, said scans being subjected to mathematic evaluation following recordal.

The duration of the IR measurement time represents a variable which is characteristic for the time resolution of the method according to the invention in respect of the detection of changes in the composition of the process stream and the associated process.

The method according to the invention is suitable for investigating long-term processes or short-term processes. An advantageous aspect of the method according to the invention is that it may be flexibly employed with regard to time: The method according to the invention may either be used for control and monitoring of long-term processes or industrial plants or it may be used for performing short-term experiments. The long-term processes are preferably in a time range of 2 weeks-2 years. The short-term processes are preferably in the range of 2 minutes to 300 hours.

Short-term processes are preferably characterized in that the deactivation of the catalyst takes place over 1-100 minutes, more preferably in a time range of 1.5-60 minutes, yet more preferably in a time range of 2-30 minutes. This results in the advantageous aspect that the training phase and the measurement phase are combined into a common training and measurement phase. This advantageous aspect of short-term investigations is of technical importance and of great utility especially in conjunction with regeneration processes. The combination with regeneration processes results from the fact that the method initially comprises a conversion process which is then followed by a regeneration process. The sequence of conversion process and regeneration process is preferably repeated, wherein the repetition is a cyclic operating mode. The number of repetitions or cycles is preferably 2, the number of cycles more preferably being 5, the number of cycles yet more preferably being 10.

The training phase and the measurement phase differ in that the process parameters are in the target parameter space during the measurement phase. When performing the training phase it is preferable when at least one process parameter exhibits a significant deviation and is not in the target parameter space.

In a preferred embodiment the method according to the invention relates to a method for high throughput testing of a multiplicity of catalysts present in process spaces arranged in parallel. The process spaces arranged in parallel are preferably reactors arranged in parallel. In this preferred embodiment it is conceivable that the deviation of the process parameter is accomplished by performing the method with reactors arranged in parallel, wherein the variation of the process parameter is effected by filling the reactors arranged in parallel with different catalyst materials and/or with different amounts of catalyst material. Thus, in this preferred embodiment of the method, the deviation or the variation of the process parameter may be generated within the system. The performance of the method and the calibration during the training phase comprised therein are also illustrated with the aid of experimental example A.2 which relates to the upgrading of aromatics mixtures.

The method described in example A.2 was performed with four different catalysts, wherein the conversion process was initially performed such that all four different catalysts were stored at the same temperature. The calibration measurements were thus further deepened by performing measurements at different temperatures. The process parameter catalyst and the process parameter temperature were accordingly varied to collect sufficient data during the training phase.

It is thus preferable when the training phase comprises undertaking both GC characterizations and IR characterizations of the process stream when individual selected process parameter spaces are present. The duration of the GC method depends inter alia on the complexity of the process stream composition and the desired target resolution in respect of the individual components. The duration of the training phase is thus decisively determined by the duration of the GC method.

It is preferable when 4 or more chromatograms are recorded during the training phase, the number of chromatograms during the training phase more preferably being 8, the number of chromatograms during the training phase yet more preferably being 15.

A further parameter which is characteristic for the method according to the invention is the ratio of IR measurements to GC measurements. Preferably the ratio of IR measurements to GC measurements is ≥6, more preferably the ratio of IR measurements to GC measurements is ≥60, yet more preferably the ratio of IR measurements to GC measurements is ≥90, yet still more preferably the ratio of IR measurements to GC measurements is ≥120.

EXAMPLES

A.1 Conversion of Methanol to Olefins

Investigations into the catalytic conversion of methanol to olefins were performed to illustrate the method according to the invention. The investigations were performed using a high-throughput apparatus for catalyst testing which was assemblable with up to 16 reactors arranged in parallel.

The schematic construction of the apparatus is shown in FIG. 9, wherein the apparatus shown in the figure comprises five reactors arranged in parallel (11)-(15). The output conduits (21)-(25) of the reactors are connected to a multiport valve (33) leading to a process stream conduit (35) which is in operative connection with an online IR spectrometer (2) and an online gas chromatograph (1). Both the online IR spectrometer (2) and the online gas chromatograph (1) are connected to the apparatus process control means. Testing employed two different zeolite-containing catalyst samples which are commercially available and are referred to as sample C1 and sample C2 in the context of the description. It is apparent from FIG. 9 that the process control unit (4), connected to the online IR (2) and the online GC (1), is in operative connection with each of the individual reaction spaces (11)-(15). The operative connection to the process control unit (4) for the reactant supply, which is preferably also connected to the process control unit (4), is not shown.

Sample C1 contained a catalyst based on SAPO-34 and sample C2 contained a catalyst based on ZSM-5. To prepare the catalytic investigations the individual catalyst samples were each mixed with quartz powder and introduced into tubular reactors in the form of dumped powder beds. The amount of catalyst samples employed was 0.92 g or 1.85 g. A total of four catalyst-containing sample mixtures were accordingly prepared. For comparative purposes two reactors were laden with quartz powder free from catalyst as inert material.

The employed reactors had a tube length of 30 cm and an internal diameter of 15 mm.

Employed as the online gas chromatograph (1) was a Hewlett Packard HP 5890 chromatograph equipped with a fused silica column (having a length of 20 m) and an FI detector. Employed as online IR spectrometer (2) was an FTIR spectrometer from BRUKER which was optimized for the MIR spectral range in a wavenumber range of 7000-400 $cm^{-1}$. The optics of the instrument were controlled with an He—Ne— laser. The beam path of the spectrometer was equipped with a heatable gas measuring cell having an internal volume of 500 mL and an optical beam length of 75 cm. During the investigations the measuring cell was heat treated at a temperature of 180° C.

When supplying the methanol-containing reactant stream a distinction was made between the following two metering procedures:

Metering procedure 1. Continuous (quasi-continuous) metering of the methanol-containing carrier gas stream over a duration in the range of 3-30 min and Metering procedure 2. Pulsed metering of the methanol-containing carrier gas stream over a duration in the range of 5-60 seconds.

After termination of the reactant stream supply an oxygen-containing gas stream was supplied to the reaction space in order to burn off the coke formed and to regenerate the catalyst.

The method for converting the methanol-containing carrier gas stream was performed according to the method of the invention. Initially a training phase was performed. During this training phase the reactor spaces were consecutively subjected to three different reactant gas streams, each having a lower reactant content than the reactant gas stream intended for the target parameter space. The reactant content in the reactant gas stream was adjusted by varying the gas loading defined by the WHSV (weight hourly space velocities). The gas loadings chosen for the training phase were characterized by the following three values of the WHSV: $0.2\ h^{-1}$, $0.3\ h^{-1}$, $0.4\ h^{-1}$.

During the different metering procedures performed during the training phase, both gas chromatographic analyses using online gas chromatograph (1) and spectroscopic analyses using online spectrometer (2) were performed on the individual process streams successively discharged from the reaction spaces into the process gas conduit (35) via the multiport valve (33).

The individual analytical results obtained by means of the different methods—i.e. by spectroscopy and by gas chromatography as a function of time and experimental test parameters—were related to one another by mathematical models. For example the GC analyses were used quantitatively to determine the respective amount of individual substances in the process stream (for example the content of methanol, dimethyl ether, methane, ethane, ethene, . . . ) and the amount of substance groups in the process stream was also determined (for example the content of aromatics, olefins, . . . ).

In the present case a proprietary model based on the PLS (partial least-squares) method was used for quantification for 9 individual substances, wherein 15 components sufficiently elucidated the variance. The wavenumbers were reduced to the ranges 423-1040 $cm^{-1}$ and 1244-2704 $cm^{-1}$ since especially the range between 1040-1244 $cm^{-1}$ and 2700-3100 $cm^{-1}$ reached the absorption limit at the employed concentration range, thus preventing further data evaluation. A finer or more precise adjustment of the optical path length to the concentration range should also allow these ranges of wavenumber to be integrated into the evaluation model.

The training phase was followed by investigations in the context of the production phase which were carried out in the presence of a reactant gas stream having a higher gas loading compared to the training phase, namely under conditions in the target parameter space.

The investigations during the production phase/measurement phase were here characterized by a gas loading at which the WHSVs were in the range of 2-20 $h^{-1}$, wherein the analytical characterization of the process stream (or the process streams) was by means of an online IR spectrometer (2) (presently optimized for the MIR range). Measurement signals were recorded at time intervals of 5 seconds to characterize the process stream. The quantitative evaluation of the band regions using the model established during the training phase made it possible to draw conclusions about the concentration of individual substances using the spectra. Trained models accordingly made it possible to predict the concentration of individual substances using the IR spectra.

To check the data analytical characterizations of the process stream were furthermore performed simultaneously with the IR measurements at intervals of in each case 20 minutes using the gas chromatograph (1) during the measurement phase. When performing so-called pulse experiments or pulse metering the additional performance of gas chromatographic analyses was completely dispensed with. An overview of the tests performed is shown in Table 1. Three experiments were performed during the training phase and five experiments were performed during the measurement phase.

When converting methanol to olefins the gas loading during the training phase was chosen such that the WHSV values were 0.2 $h^{-1}$, 0.3 $h^{-1}$ and 0.4 $h^{-1}$. During the measurement phase the WHSV values were 5 $h^{-1}$, 8 $h^{-1}$, 12 $h^{-1}$, 16 $h^{-1}$ and 20 $h^{-1}$. The process streams were thus generated and then also characterized as a function of time during the training phase and are characteristic of the three different parameter spaces and selected process parameters. Whether these three different parameter spaces are sufficient depends, among other things, on the process being studied and the temporal behavior of the process being studied.

It is preferable in connection with the method according to the invention that a number of process parameters spaces which is preferably 2 is investigated during the training phase. The number of process parameter spaces employed for generation and characterization of process streams when performing the training phase is more preferably 3, the number of process parameter spaces yet more preferably being 4.

When performing the measurement phase the parameter space of the WHSV is preferably in the range of >1 $h^{-1}$ to 20 $h^{-1}$. By contrast, during the training phase the parameter space of the WHSV is preferably in the range of 0.1 $h^{-1}$ to 1 $h^{-1}$. During performance of the measurement phase the employed WHSV range may also be regarded as a target parameter space.

In example A.1 the WHSV is significantly outside the target parameter space during the training phase.

Having regard to the lower limit of the target parameter space (i.e. a WHSV of 5 $h^{-1}$) during the measurement phase the deviation of the process parameter WHSV during the training phase is only 8% compared to the measurement phase. This gives rise to the requirement that the process parameters, or at least one process parameter, are outside the target parameter space during the training phase. The term "outside the target parameter space" is to be understood as meaning that—when comparing the training phase and the measurement phase—the deviation of at least one process parameter is ≥10%, the deviation preferably being ≥20%, the deviation more preferably being ≥50%, the deviation especially preferably being ≥75%.

Having regard to A.1 the lower limit of the WHSV in the target parameter space was given by a WHSV of 5 $h^{-1}$. The WHSV during the training phase was 0.4 $h^{-1}$. The deviation was therefore 4.6 $h^{-1}$ which corresponds to a percentage deviation of 92%. Having regard to the upper limit of the target parameter the deviation is given by a WHSV difference of 19.6 $h^{-1}$ which corresponds to a percentage deviation of 98%.

Table 1 gives an overview of the test numbers and the associated process parameters.

| Experiment number | WHSV [$h^{-1}$] | Temp. [° C.] | Operating mode | Phase |
|---|---|---|---|---|
| C1_01 | 0.2 | 400 | continuous | training phase |
| C1_02 | 0.3 | 400 | continuous | training phase |
| C1_03 | 0.4 | 400 | continuous | training phase |
| C1_04 | 5 | 400 | continuous | measurement phase |
| C1_05 | 8 | 400 | continuous | measurement phase |
| C1_06 | 12 | 400 | continuous | measurement phase |
| C1_07 | 16 | 400 | continuous | measurement phase |
| C1_08 | 20 | 400 | continuous | measurement phase |

Table 2 shows the percentage of the variance covered by the model according to the components (factors).

| A. 2 Method for upgrading of aromatics mixtures | | | | | | | | | |
|---|---|---|---|---|---|---|---|---|---|
| Components | ethene | propene | butene | methane | ethane | propane | butane | methanol | DME |
| 1 | 0.405 | 7.72 | 59.059 | 28.49 | 89.47 | 52.08 | 47.89 | 22.06 | 70.82 |
| 2 | 75.92 | 92.01 | 79.86 | 28.91 | 89.49 | 89.06 | 86.22 | 22.22 | 91.81 |
| 3 | 94.5 | 94.05 | 96.05 | 40.55 | 89.95 | 97.31 | 96.56 | 25.23 | 96.66 |
| 4 | 94.78 | 97.52 | 98.9 | 94.36 | 89.96 | 98.69 | 97.86 | 36.79 | 99.22 |
| 5 | 96 | 98.65 | 99.24 | 95.75 | 90.27 | 98.86 | 97.88 | 94.43 | 99.23 |
| 6 | 98.94 | 99.09 | 99.5 | 96.08 | 97.36 | 99.08 | 99.03 | 95.55 | 99.43 |
| 7 | 99.12 | 99.11 | 99.67 | 98.06 | 97.38 | 99.09 | 99.38 | 95.58 | 99.66 |
| 8 | 99.13 | 99.19 | 99.72 | 98.18 | 97.88 | 99.53 | 99.47 | 95.65 | 99.66 |
| 9 | 99.13 | 99.32 | 99.73 | 98.42 | 98.7 | 99.53 | 99.47 | 95.67 | 99.72 |
| 10 | 99.13 | 99.34 | 99.75 | 98.65 | 98.79 | 99.62 | 99.55 | 95.67 | 99.73 |
| 11 | 99.17 | 99.35 | 99.75 | 98.69 | 98.84 | 99.69 | 99.55 | 95.8 | 99.73 |
| 12 | 99.17 | 99.37 | 99.77 | 98.89 | 99.33 | 99.71 | 99.63 | 95.8 | 99.73 |
| 13 | 99.17 | 99.38 | 99.78 | 98.89 | 99.34 | 99.71 | 99.65 | 95.8 | 99.73 |
| 14 | 99.19 | 99.38 | 99.78 | 98.89 | 99.34 | 99.71 | 99.65 | 95.83 | 99.73 |
| 15 | 99.22 | 99.4 | 99.78 | 98.89 | 99.34 | 99.72 | 99.7 | 95.98 | 99.73 |

Catalytic investigations into the upgrading of aromatics mixtures were also performed to illustrate the method according to the invention. For comparability of catalysts it is in many cases of interest to operate them under process conditions selected such that the different catalysts and processes result in identical target parameters. In numerous processes this target parameter is conversion. In naphtha reforming the target parameter is octane number.

This target parameter is achieved for example by alteration of the process parameters such as temperature, pressure, WHSV etc. Especially when operating the method according to the invention in a parallel arrangement in which a multiplicity of catalysts is investigated simultaneously and in parallel the method according to the invention results in advantages. In a preferred embodiment the method also relates to adjustment of the target parameter to a fixed value or, in connection with an apparatus having a multiplicity of reactors arranged in parallel, the respective adjustment of the target parameters in the processes performed in parallel. In the cases where deactivation of the catalyst occurs the method also relates to readjusting the process to achieve and maintain the target parameter despite the occurrence of deactivation.

In connection with the method it is important that adjustment and readjustment is carried out faster than the change in the product spectrum and the deactivation of the catalysts over time. One advantage of the method according to the invention is also that performance of the online IR measurements during the measurement phase allows precise and rapid analysis and thus also ensures rapid readjustment.

In the present example the method according to the invention was illustrated in connection with a catalytic method for converting and upgrading an aromatics mixture. The employed aromatics mixture was a mixture of mononuclear aromatics having different numbers of alkyl substituents and positions of the alkyl substituents. The objective of the method was that of producing a product having a high proportion of p-xylene. The method was performed in such a way that the conversion of aromatics was selected as a target parameter. The investigations were performed using an apparatus for catalyst testing which was equipped with four reactors arranged in parallel. Each of the four reactors arranged in parallel was filled with another catalyst material referred to hereinbelow as catalyst K1-K4.

In a first method variant the analysis of the process stream was carried out exclusively with an online gas chromatograph (1), wherein the spectra were evaluated automatically and the conversion determined. The duration of the individual gas chromatographic analysis was approximately 30 minutes. In order to sequentially characterize the process streams of the four reactors arranged in parallel using the one online gas chromatograph (1) a duration of 2 hours was required to obtain one measured value per process stream.

The four reactors arranged in parallel comprising the catalysts K1 to K4 were initially started up isothermally at the same temperature to obtain initial information about the relationship between conversion and temperature. These measurements, carried out at identical temperature, were deepened by additional measurements at different temperatures to obtain a calibration function showing the relationship between conversion and temperature. The results of the investigation are shown in FIG. 7, wherein the lower portion shows temperature as a function of the TOS (TOS=Time On Stream) and the upper portion shows conversion as a function of the TOS. Adjustment to a target value for conversion taking account of this calibration function commences from a TOS of 6 hours, wherein the result from the gas chromatic analysis is automatically transferred to the process control means and the temperature adjusted. It is apparent that the same conversion is achieved after about 3 cycles, each of 2 h in length, and actual measurement of the catalysts may be carried out at identical conversion. In the present case the adjustment process required about 6 hours. Performing the method with an apparatus having a higher degree of parallelization and equipped, for example, with 16 reactors would correspondingly require 16×30 min measuring time per cycle which for three cycles would result in a duration of 24 hours.

Investigations into performing the method in a second method variant are described hereinbelow. FIG. 8 shows the method according to the invention with inclusion of an online IR spectrometer (2). The initial phase, in which the reactors were operated isothermally, was used to record the calibration function. The online gas chromatograph (1) and the online IR spectrometer (2) were operated in parallel. GC chromatograms comprising the conversion information and the accompanying IR spectra were obtained. Accompanying IR spectra is to be understood as meaning that said spectra were recorded simultaneously with the GC chromatograms. The obtained measurement data contained in the GC chromatograms and IR spectra as a function of time were used to train a model by PLS. Subsequently, during adjustment to constant conversion the recordal of GC chromatograms was dispensed with. Investigation of the process streams was carried out based on recordal of online IR spectra while determining conversion using the previously established model. In this example, the measurement time was reduced from 30 minutes to 2 minutes and the target conversion was achieved within 24 minutes. In this example, the method according to the invention showed a significant speed advantage compared to a method performed not in conjunction with an online IR spectrometer. In order to obtain measurement points with a higher information density the online gas chromatograph (1) was switched on upon reaching a constant target conversion. The additional use of the online gas chromatograph (1) to characterize the process streams had the advantage that the determination of selectivities was further improved. Online IR spectroscopy provided the control parameter, wherein in the present case conversion was used as the control parameter. An improved determination of the selectivities made it possible to improve the differentiation of the catalysts.

The method for upgrading aromatic mixtures presently described by way of example may in the same way be used as a method for transalkylation reactions, for the dealkylation of ethylbenzene, for the disproportionation of toluene, for the isomerization of xylenes and in other processes.

BRIEF DESCRIPTION OF THE FIGURES

FIG. 2 top panel: Yields from gas chromatographic analysis; FIG. 2 lower panel: predicted yields from MIR spectra.

LIST OF REFERENCE NUMERALS

Figure 1:
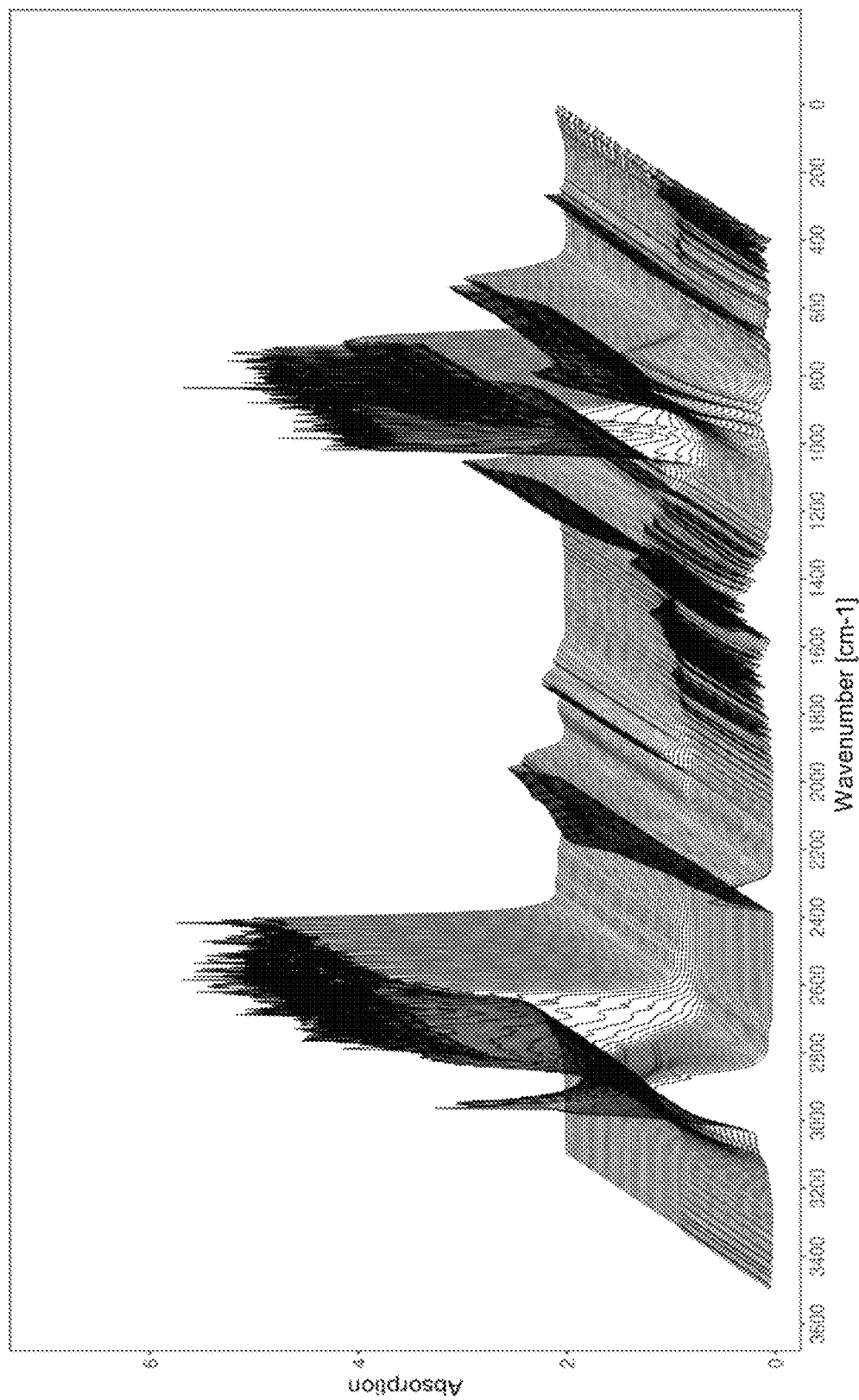
FIG. 1 shows a series of MIR spectra, which were recorded at a WHSV of 0.4 $h^{-1}$ during the training phase of the method. The method step is characterized with the number Experiment C1_03 in table 1. The time intervals for the recording of the spectra were 5 seconds, wherein the spectra recorded over a period of several minutes are shown.
Figure 2:
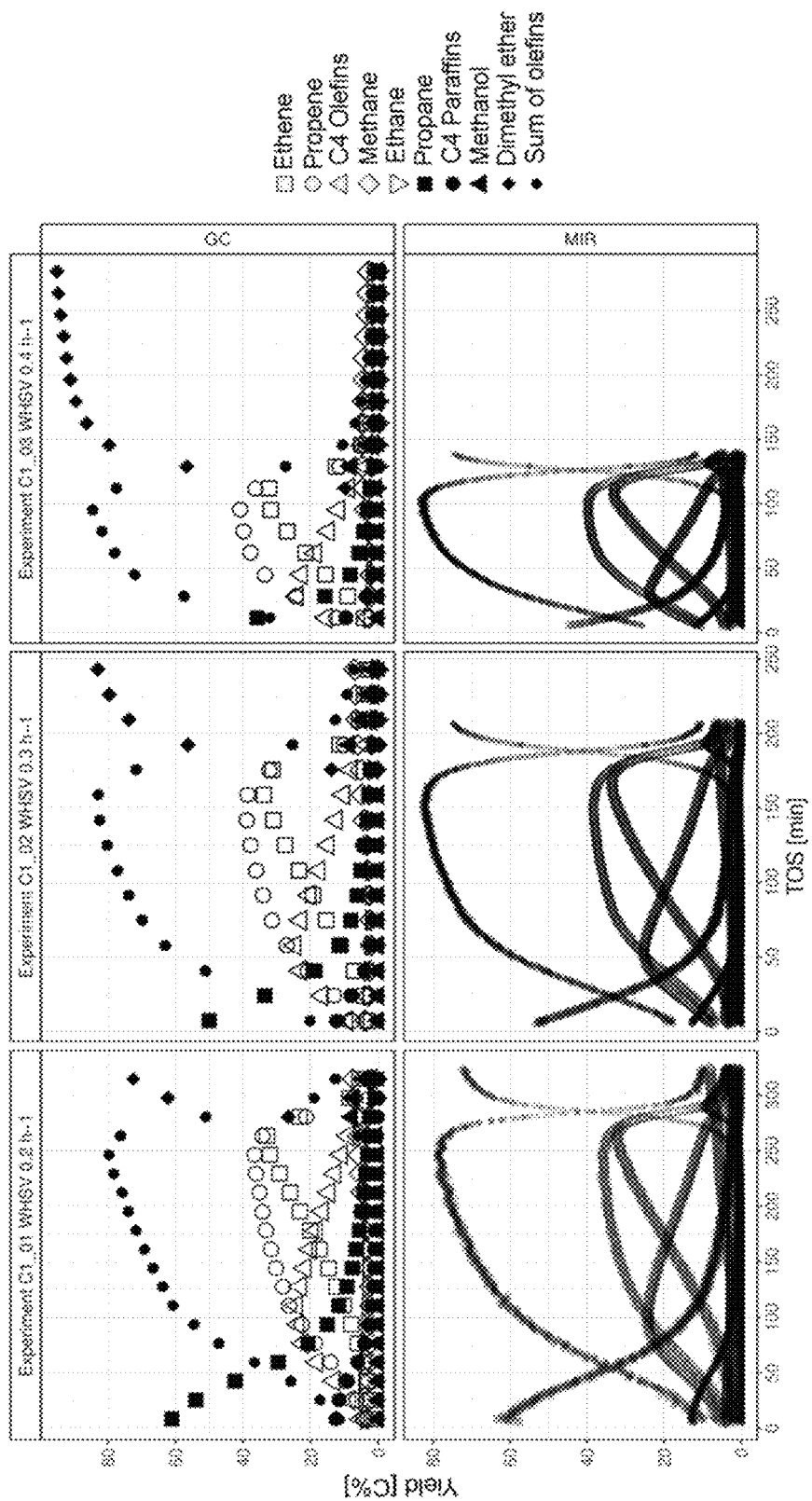
FIG. 2 shows the composition of the process stream as a function of time which had been determined by GC at three different gas loads during the training phase and which had been calculated for MIR spectra. The WHSVs were 0.2 $h^{-1}$, 0.3 $h^{-1}$ and 0.4 $h^{-1}$ and were recorded in the experiments having the test numbers C1_01, C1_02 and C1_03.
Figure 3:
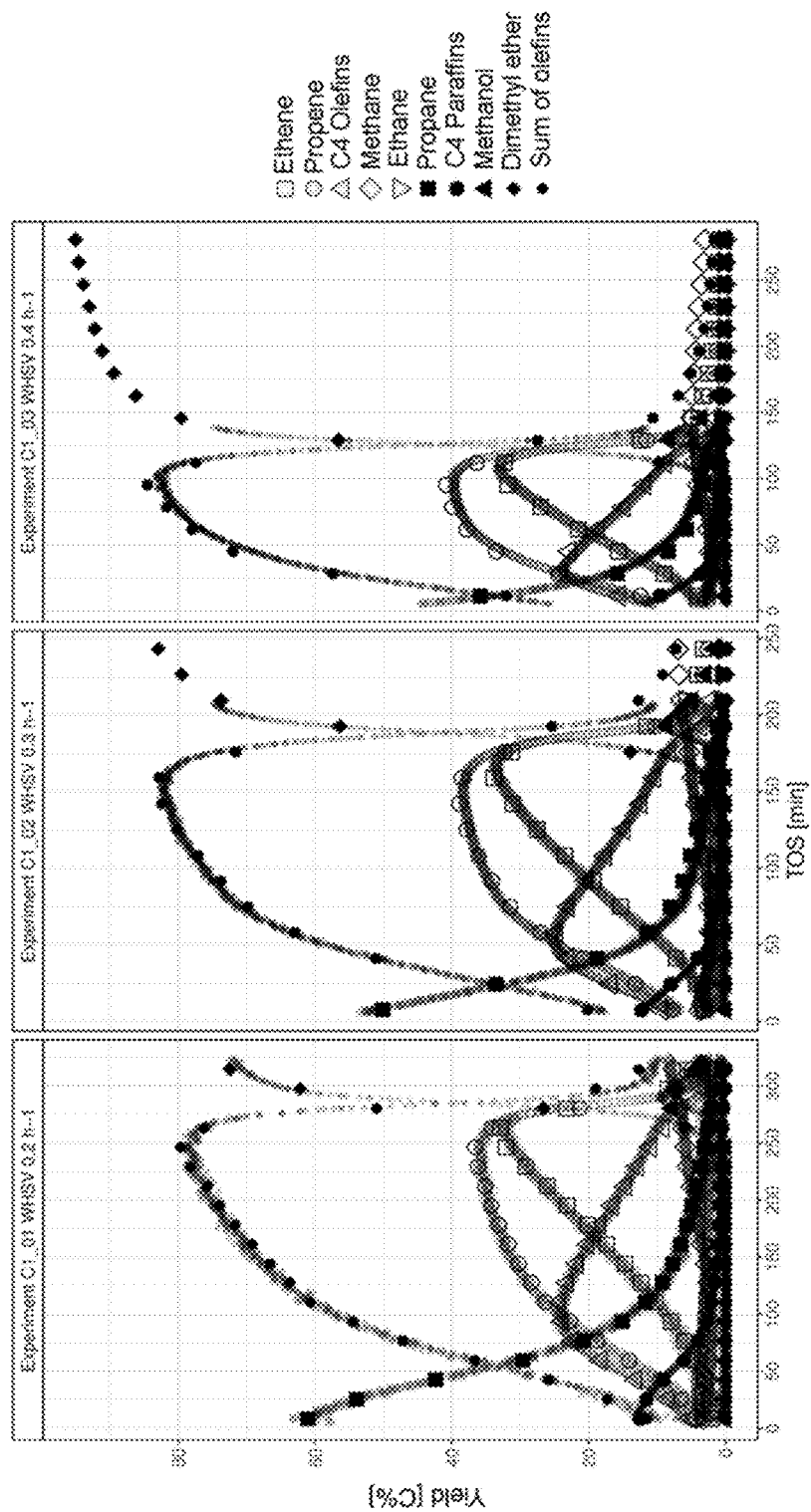
FIG. 3 shows data acquired during the training phase at low WHSVs, namely in a superimposed representation of GC and MIR data. The large symbols characterize the yields determined by gas chromatographic analyses; the small symbols characterize the predicted yields determined from the MIR spectra.
Figure 4:
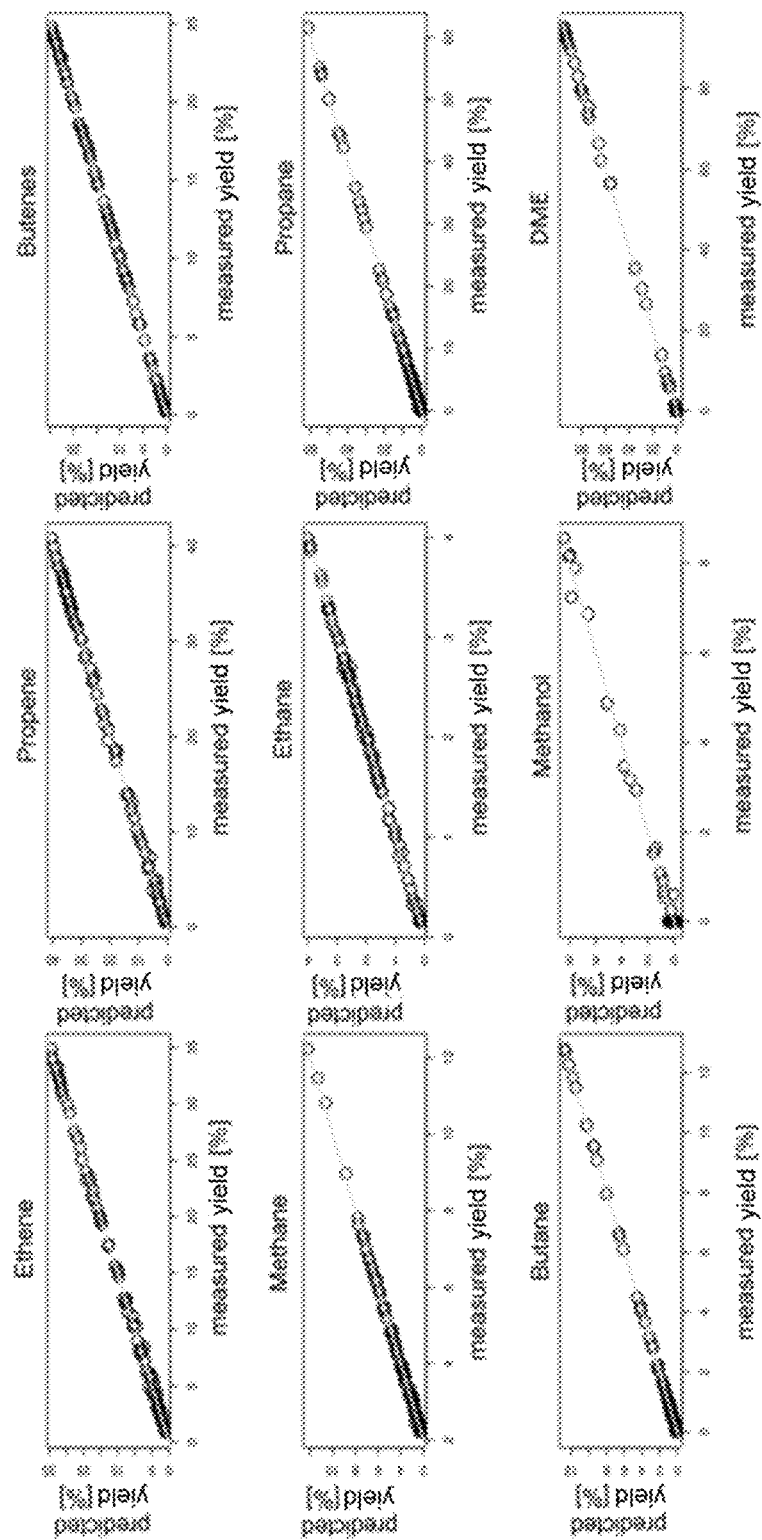
FIG. 4 shows the models obtained by relating GC data and IR data during the training phase. The predicted yields versus the measured yields are shown for 9 different individual substances.
Figure 5:
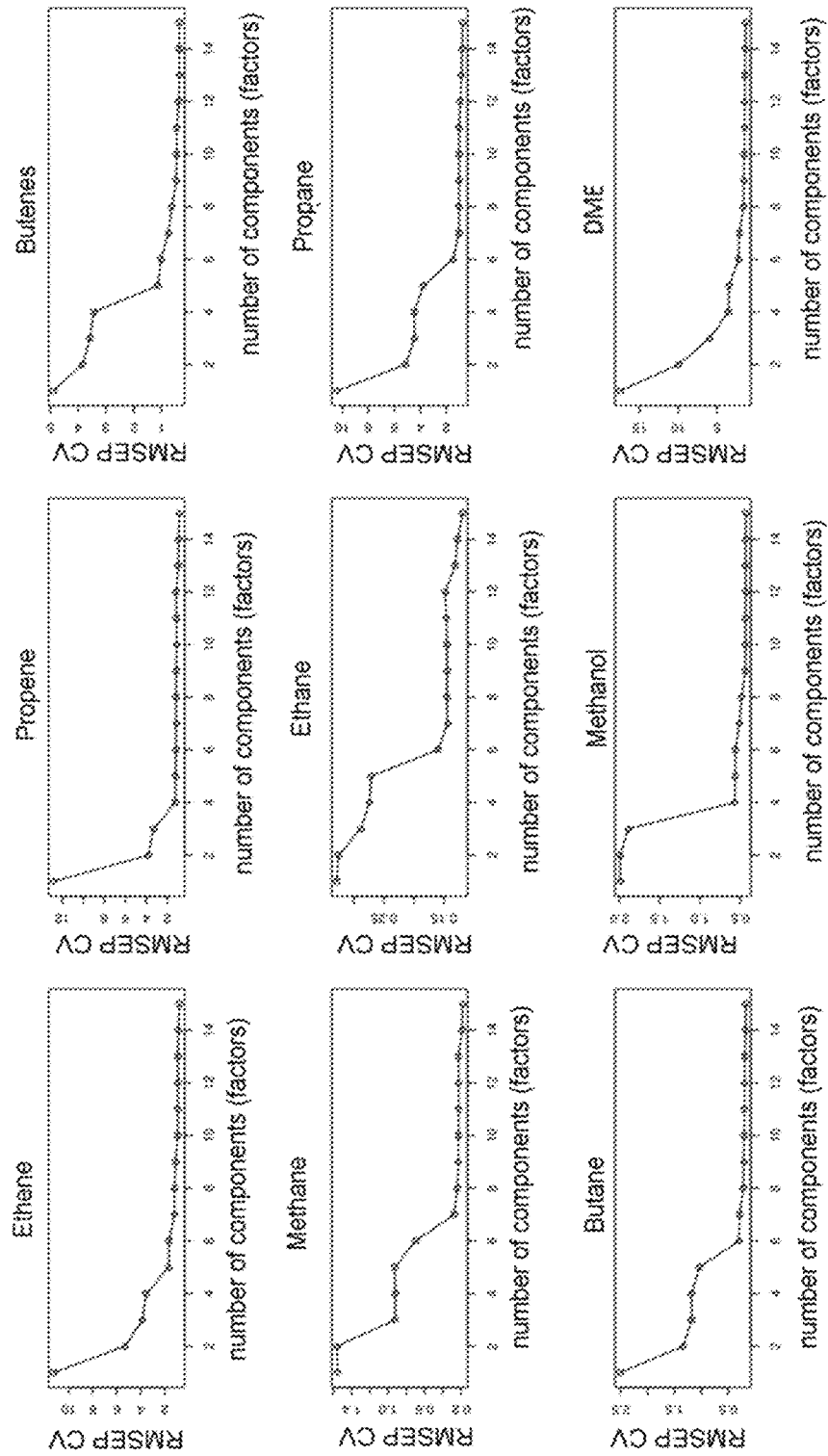
FIG. 5 shows the RMSEP (root mean square error predicted) of the cross-validation for the trained models of the 9 different individual substances against the number of components, wherein up to 15 components were used.
Figure 6:
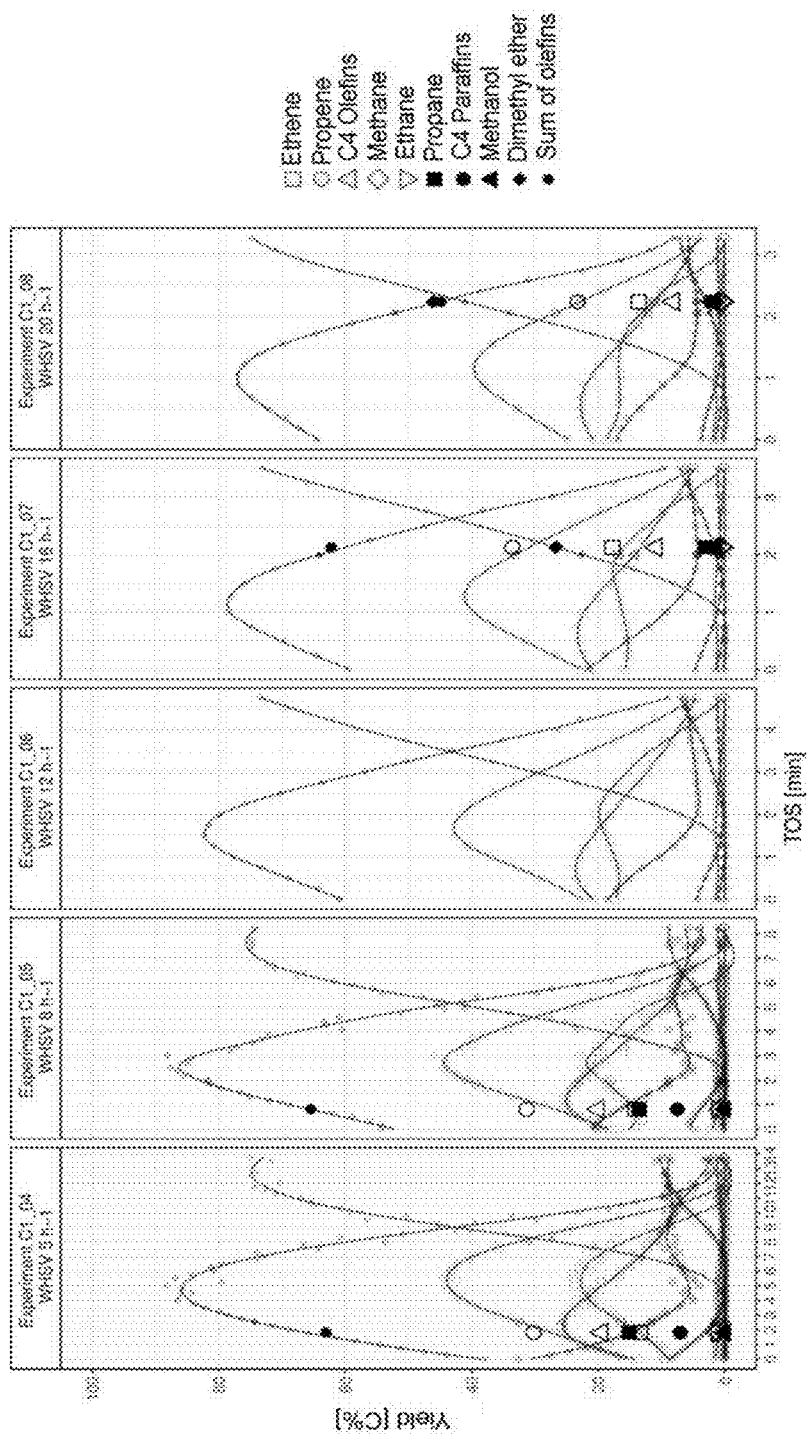
FIG. 6 shows the yields from the MIR spectra predicted during the production phase for WHSVs in the target parameter space (i.e. there were high WHSVs of 5, 8, 12, 16 and 20 h$^{-1}$ in five experiments). The large symbols represent yields from the gas chromatographic analysis, the small symbols represent predicted yields from the MIR.
Figure 7:
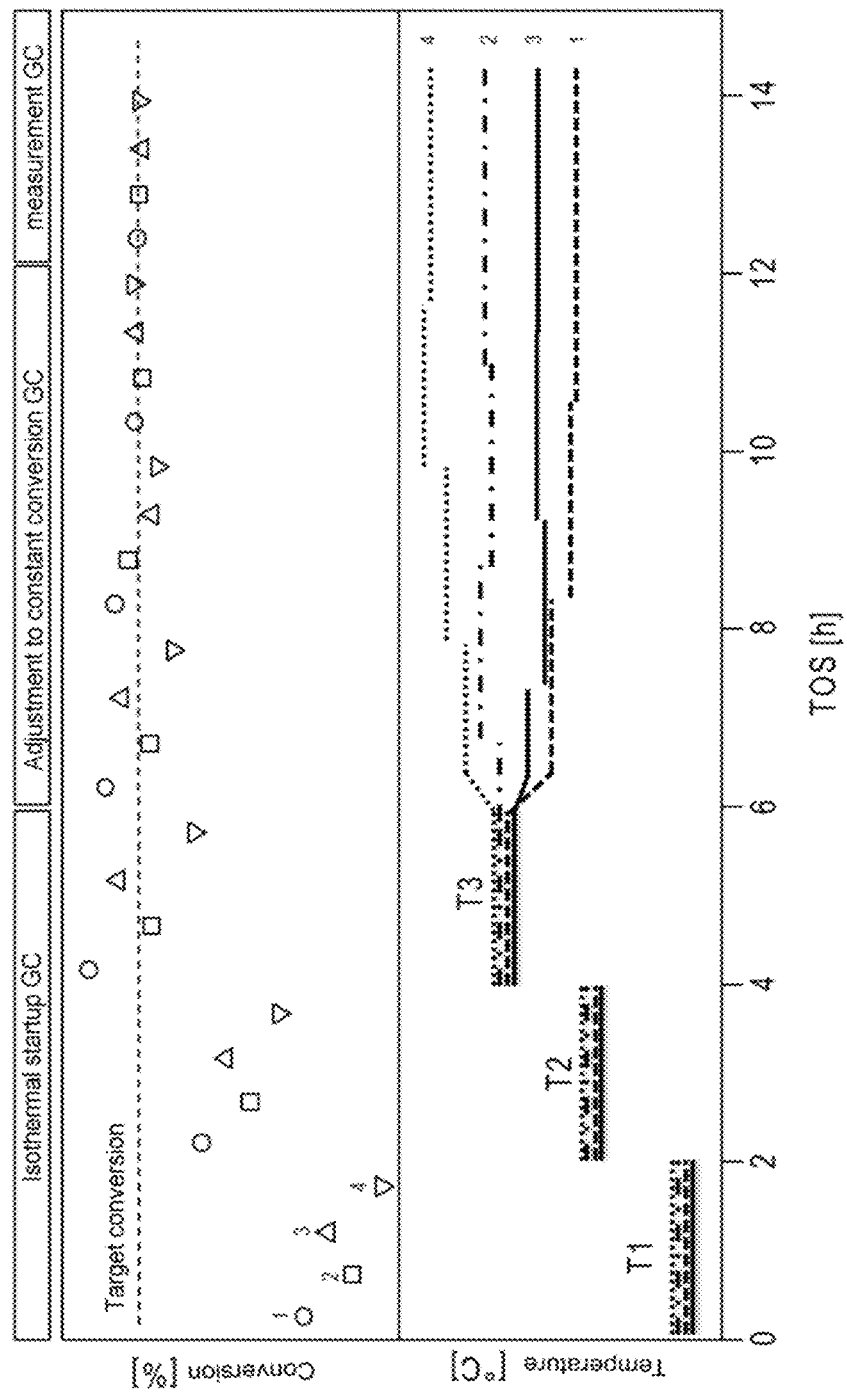
FIG. 7 shows values for conversion and temperature as a function of the time-on-stream (TOS) obtained when performing a method for converting aromatics in which 4 catalysts were arranged in a reactor system with 4-fold parallelization. Conversion is shown at the top and reactor temperature at the bottom. Conversion was determined solely by gas chromatograph.
Figure 8:
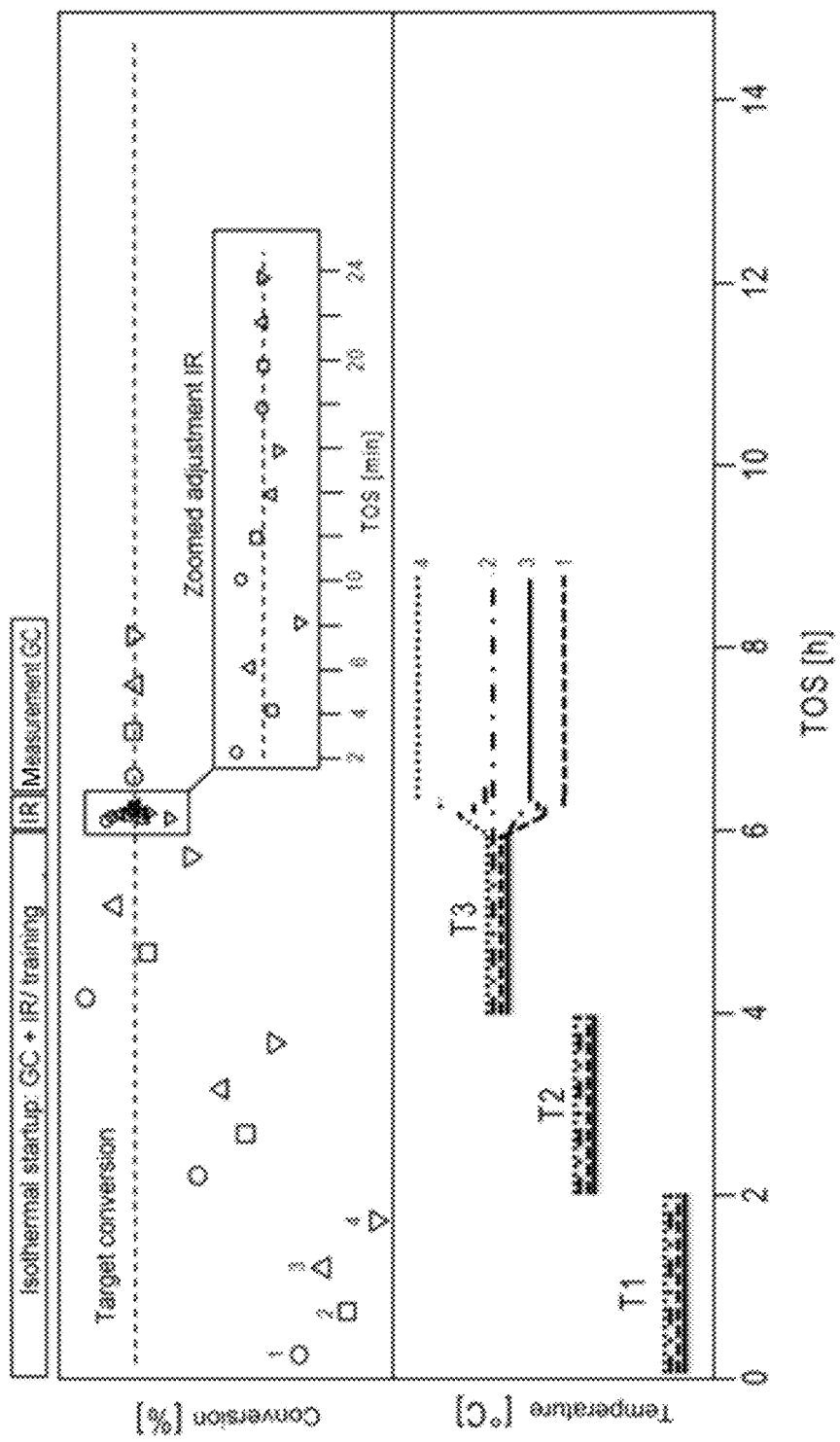
FIG. 8 shows values for conversion and temperature as a function of the time-on-stream (TOS) obtained when performing a method according to the invention in which four catalysts were investigated in four reactors arranged in parallel. Conversion is shown at the top and reactor temperature at the bottom. Conversion was determined using an online gas chromatograph (1) and adjustment to constant conversion was performed using an online IR spectrometer (2).
Figure 9:
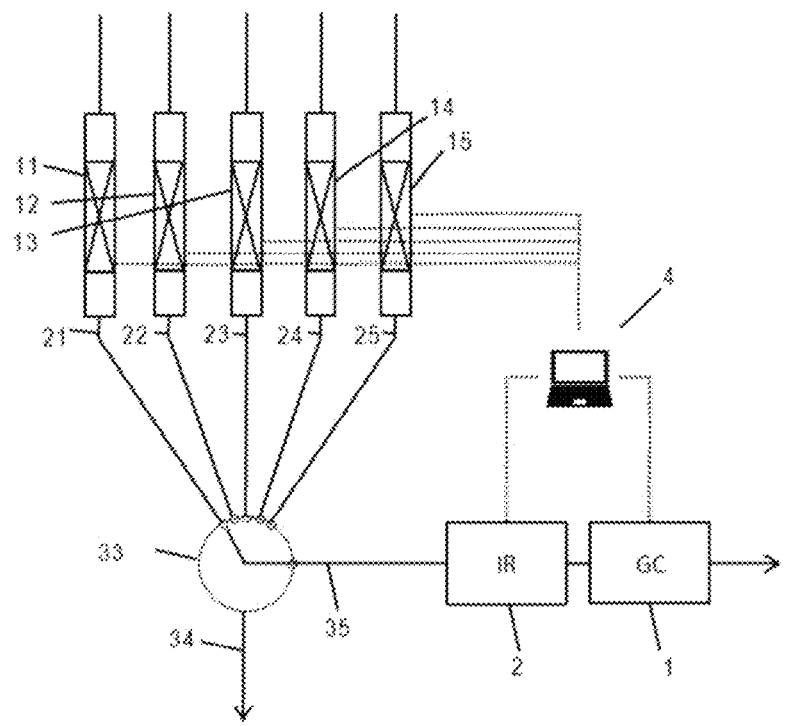
FIG. 9 shows a schematic representation of the apparatus according to the invention in an embodiment equipped with five reaction spaces (11)-(15) arranged in parallel, wherein the online spectrometer (2) and the online gas chromatograph (1) are serially arranged in the process stream conduit (35) and the process control unit (4) is coupled to the reaction spaces.
Figure 10:
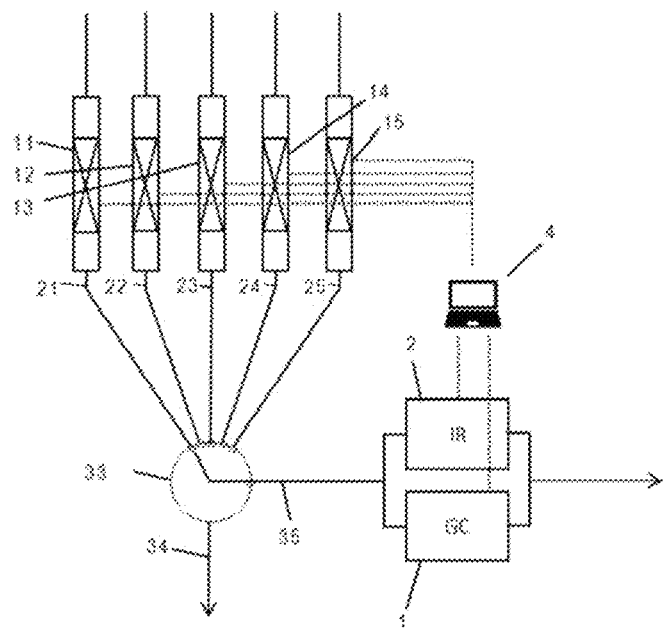
FIG. 10 shows a schematic representation of the apparatus according to the invention in an embodiment which corresponds to the embodiment shown in FIG. 9, wherein the process stream conduit (35) is divided into two conduits and the online IR (2) and the online GC (1) are arranged in parallel in these two conduits.

| | | |
|---|---|---|
| 1 | — | online GC, online gas chromatograph |
| 2 | — | online IR, online IR spectrometer or online spectrometer, preferably optimized for the MIR range |
| 4 | — | Process control unit |
| 35 | — | Process stream conduit |
| 34 | — | Waste air conduit |
| 33 | — | Multiport valve |
| 21, 22,-25 | — | Reaction space output-side process gas conduits connected to multiport valve |
| 11, 12,-15 | — | Process spaces, preferably reaction spaces, more preferably tubular reactors |

The invention claimed is:

1. A method for investigating at least one process stream comprising at least five different hydrocarbon-containing components, wherein the method comprises at least the steps of:
   a) providing at least one process stream conduit which is in operative connection with at least one online IR spectrometer and in operative connection with at least one online gas chromatograph;
   b) passing at least one process stream through the at least one process stream conduit, wherein during this passing of the process stream through the process stream conduit an analytical characterization of the process stream using an online IR spectrometer and an online gas chromatograph is performed;
   c) evaluating the spectral data obtained in the analytical characterization of the process stream using an online IR spectrometer as a function of the time at which this spectroscopic analysis of the process stream was carried out;
   d) evaluating the chromatography data obtained during the analytical characterization of the process stream using the online gas chromatograph as a function of a sampling time for samples taken from the process stream;
   e) machine learning-based training of a model that models a mathematical relationship between spectral data and corresponding chromatography data in respect of an identical process stream by using the evaluation results obtained in steps c) and d) in respect of the process stream passed through the process stream conduit in step b).

2. The method according to claim 1, wherein steps c)-e) are performed and at least one reaction parameter is altered in relation to the same reaction parameter as set in steps a) and/or b), wherein this parameter is preferably selected from: WHSV, temperature, total pressure and/or partial pressure of reactants.

3. The method for investigating at least one process stream according to claim 1, wherein it comprises at least two different phases, wherein one phase is a training phase comprising steps a) to e) and the second phase is an actual measurement phase in which an analytical characterization of a process stream passed through the at least one process stream conduit is carried out using the online IR spectrometer on the basis of the model trained in the training phase.

4. The method for investigating at least one process stream according to claim 1, wherein the process stream passed through the process stream conduit is a gaseous process stream, the temperature of the gaseous process stream being in the range of 20-350° C.

5. The method for investigating at least one process stream according to claim 1, wherein the online gas chromatograph and the online IR spectrometer are serially arranged in respect of the process stream conduit and the temporal offset is in the range of 1 sec to 180 sec.

6. The method for investigating at least one process stream according to claim 1, wherein the analysis units, the online gas chromatograph and the online IR spectrometer, are coupled to a common process control unit, wherein the process control unit is in operative connection with a process space and controls, governs or regulates the process proceeding in the process space.

7. The method for investigating at least one process stream according to claim 6, wherein the process control unit regulates the process such that the product structure is controlled by adapting a process operating parameter.

8. The method for investigating at least one process stream according to claim 1, wherein the process comprises at least one process from the group selected from methanol conversion processes such as MTO (methanol to olefins), dehydrogenation reactions such as propane dehydrogenation, coupling reactions such as methane coupling, naphtha reforming and processes for conversion of aromatics.

9. The method for investigating at least one process stream according to claim 1, wherein the online IR spectrometer (2) operates in the mid IR range (MIR) and the wavenumbers are in the range of 400 cm$^{-1}$-3500 cm$^{-1}$.

10. The method for investigating at least one process stream according to claim 1, wherein the model or the method as employed in step e) comprises a statistical method selected from the group of multivariate analyses such as principal component analysis (PCA), partial least squares (PLS) regression, principal component regression (PCR), multi-linear regression (MLR) analysis, discriminant analysis or neural networks.

11. The method for investigating at least one process stream according to claim 1, wherein additional data for training the model, provided for according to steps c) to e), are obtained by variation of process parameters such as temperature, pressure, partial pressure of the reactants or WHSV.

12. The method for investigating at least one process stream according to claim 1, wherein the mass of the catalyst employed for the process is in the range of 0.1-200 ccm.

13. The use of the method according to claim 1 in high-throughput testing of at least four catalysts arranged in parallel reactors.

14. The method for investigating at least one process stream according to claim 7, wherein the product structure is being controlled in such a way that octane number is constant, that selectivity is constant or that conversion is constant.

15. The method for investigating at least one process stream according to claim 7, wherein regulation is being undertaken by altering parameters from the group of temperature, WHSV.

* * * * *